United States Patent

Masuda et al.

[11] Patent Number: 5,500,696
[45] Date of Patent: Mar. 19, 1996

[54] OPHTHALMIC APPARATUS INCLUDING AN APPARATUS CONTROL MECHANISM HAVING MULTIPLE MODES

[75] Inventors: Takashi Masuda, Yamato; Toshiaki Okumura, Yokohama; Koji Uchida, Yokohama; Osamu Yamamoto, Yokohama, all of Japan

[73] Assignee: Canon Kabushiki Kaisha, Tokyo, Japan

[21] Appl. No.: 265,138

[22] Filed: Jun. 24, 1994

[30] Foreign Application Priority Data

Jul. 2, 1993 [JP] Japan .................................... 5-164669

[51] Int. Cl.⁶ .................................................... A61B 3/10
[52] U.S. Cl. ........................................ 351/205; 351/212
[58] Field of Search .................................. 351/200, 205, 351/211, 212, 221

[56] References Cited

U.S. PATENT DOCUMENTS

| | | | |
|---|---|---|---|
| 4,660,946 | 4/1987 | Masuda | 351/212 |
| 4,666,269 | 5/1987 | Nakamura et al. | 351/212 |
| 4,704,012 | 11/1987 | Kohayakawa et al. | 359/480 |
| 4,710,003 | 12/1987 | Masuda et al. | 351/212 |
| 4,755,041 | 7/1988 | Ishikawa et al. | 351/211 |
| 4,764,006 | 8/1988 | Hamano et al. | 351/211 |
| 4,894,670 | 1/1990 | Masuda | 351/214 |
| 5,056,522 | 10/1991 | Matsumura et al. | 128/645 |
| 5,107,851 | 4/1992 | Yano et al. | 128/648 |
| 5,203,979 | 4/1994 | Maeda et al. | 351/212 |
| 5,270,749 | 12/1993 | Okumura | 351/211 |
| 5,414,478 | 5/1995 | Van Gelderen | 351/205 |

Primary Examiner—Anita Pellman Gross
Assistant Examiner—Huy Mai
Attorney, Agent, or Firm—Fitzpatrick, Cella, Harper & Scinto

[57] ABSTRACT

An ophthalmic apparatus includes an apparatus control mechanism for performing an ophthalmic operation for an eye to be examined, and a rotary mechanism for inputting information to the control mechanism. The control mechanism has a plurality of modes. The rotary mechanism serves as an input unit for performing different control operations respectively corresponding to the individual modes.

26 Claims, 9 Drawing Sheets

```
           SET MODE
VD      : 0.0  [12.0]  13.5  15.0
CYL     : [-]    +     +/-
INC     : [0.12]  0.25
mm/D    : [mm]  D
INDEX   : [1.3375]  1.336  1.332
DATE    : 93/06/20    12:15
ORDER   : [YMD]  MDY  DMY
     JOG   JOY   SET
      ↑↓    ⇄    [END]
```

OPHTHALMIC APPARATUS INCLUDING AN APPARATUS CONTROL MECHANISM HAVING MULTIPLE MODES

BACKGROUND OF THE INVENTION

1. Field of the Invention

The present invention relates to an ophthalmic apparatus.

2. Related Background Art

A fundus camera, an autorefractometer, a noncontact tonometer, and the like are known as ophthalmic apparatuses. Most of these apparatuses use joysticks for positioning the apparatuses relative to eyes to be examined. An independent rotary mechanism is arranged in or near the joystick and used as an input means to control vertical movement of the main body of the apparatus and the illumination light amount.

However, such a conventional rotary mechanism always has a single function as an input means. For this reason, control is often performed using a large number of switches. For example, in vertical movement control of a measuring portion using a rotary mechanism arranged in a joystick, the rotary mechanism of the joystick can control only vertical movement. For example, even if various conditions which do not require positioning of a patient are to be set in practice, independent switches are required, and the function of the rotary mechanism of the joystick is of no use during setting the above conditions. In particular, when an examiner is allowed to select a specific one of a plurality of items or an optimal one of a plurality of continuously changing states, the examiner must depress a specific switch a plurality of number of times or must keep depressing a switch for a long period of time, resulting in poor operability.

SUMMARY OF THE INVENTION

The present invention has been made in consideration of the conventional problems described above, and has as its first object to provide an ophthalmic apparatus capable of decreasing the number of switches, reducing cost, facilitating the operations, and improving operability.

Other objects, features, and advantages of the present invention will be apparent from the following detailed description in conjunction of the accompanying drawings.

DESCRIPTION OF THE PREFERRED EMBODIMENTS

Figure 1:
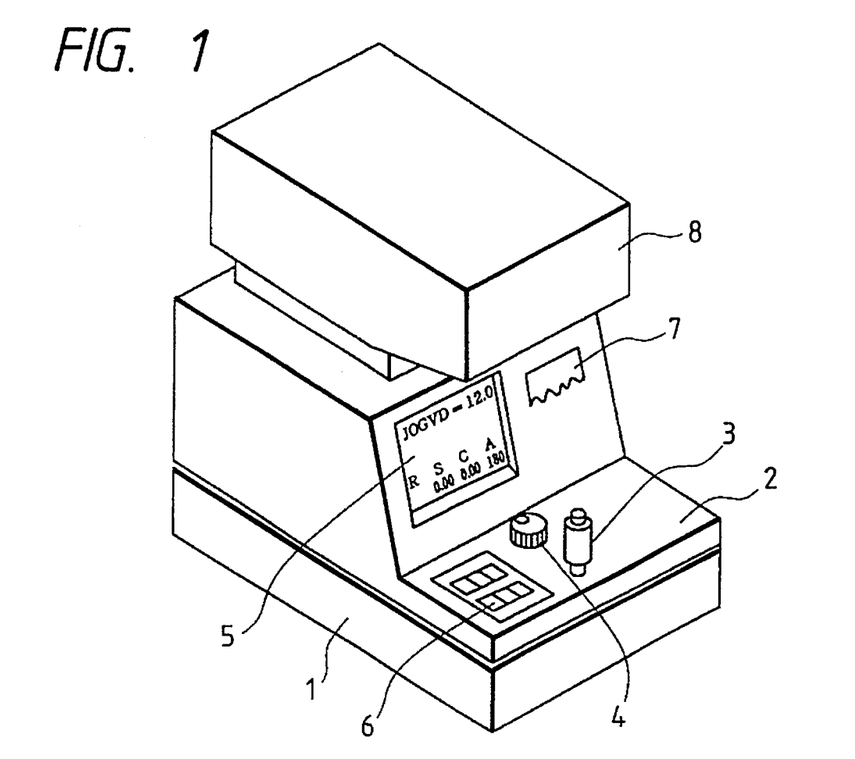
FIG. 1 is a perspective view showing an autorefkeratometer according to an embodiment of the present invention.

FIG. 1 is a perspective view showing an autorefkeratometer according to an embodiment of the present invention. This apparatus comprises a movable portion 2 moved to position an eye to be examined with respect to a stationary portion 1. The movable portion 2 includes a joystick 3 used for allowing an examiner to position the eye to be examined, a jog dial 4 for setting various conditions, a CRT monitor 5 for monitoring an anterior eye portion of the eye to be examined, and a switch panel 6 having various switches thereon. A measurement value is output to a printer 7 incorporated in the main body of this apparatus. The joystick 3 is pivoted in all directions to finely position the movable portion 2 with respect to the eye to be examined. The joystick 3 is rotated to vertically move a measurement portion 8 of the movable portion 2, thereby adjusting the height. In practice, this apparatus includes an encoder for driving and controlling a motor arranged therein. Rotation of the joystick is detected by this encoder, and the motor is driven on the basis of the detected rotation information. For example, when the joystick is rotated clockwise, the measurement portion 8 is moved upward; when the joystick is rotated counterclockwise, the measurement portion 8 is moved downward.

Figure 2:
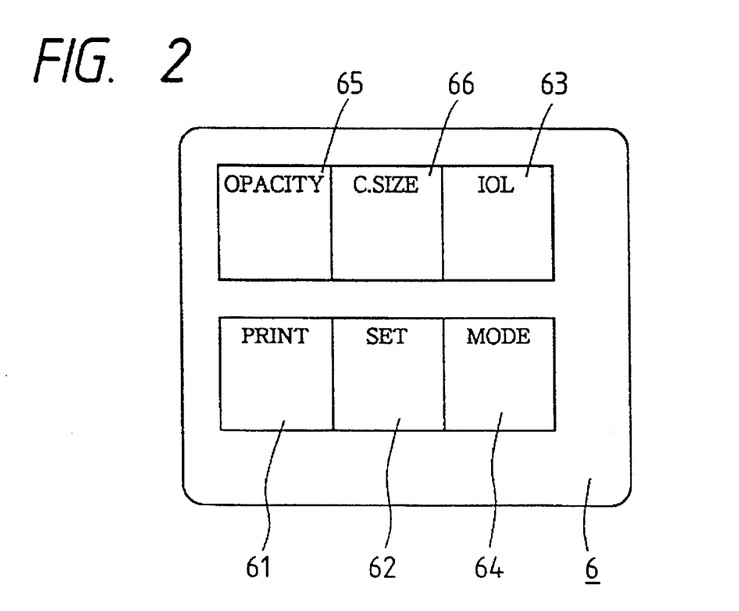
FIG. 2 is a plan view of switches arranged on a switch panel.

FIG. 2 shows the layout of switches on the switch panel 6. A print switch 61, a set switch 62 for storing various settings, an IOL switch 63 for measuring an eye inserted with an intraocular lens, a mode switch 64 for switching between an autorefractometer function and an autokeratometer function, an observation switch 65 for performing diaphanoscopy observation, and a corneal size measurement mode switch 66 for switching to a mode for measuring the diameter of a cornea are arranged on the switch panel 6.

Figure 3:
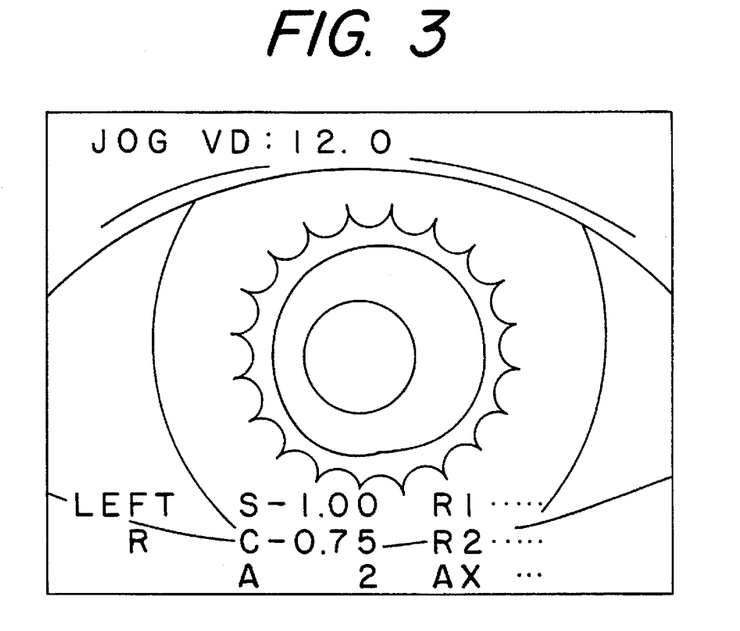
FIG. 3 is a view showing a measurement screen.

FIG. 3 is a view showing the screen on the CRT monitor 5 in the refractive index measurement of the autorefkeratometer. In this state, the jog dial 4 functions as an input means for changing the distance between vertices. "JOG VD:12.0" indicates to the examiner that the distance between the vertices can be changed by rotation of the jog dial 4, and also indicates that the current distance between the vertices is 12.0. In practice, when the jog dial 4 is rotated clockwise, the distance between the vertices is toggled in an order of 0.0, 12.0, 13.5, and 15.0. When the jog dial 4 is rotated counterclockwise, the toggling order is reversed.

Figure 4:
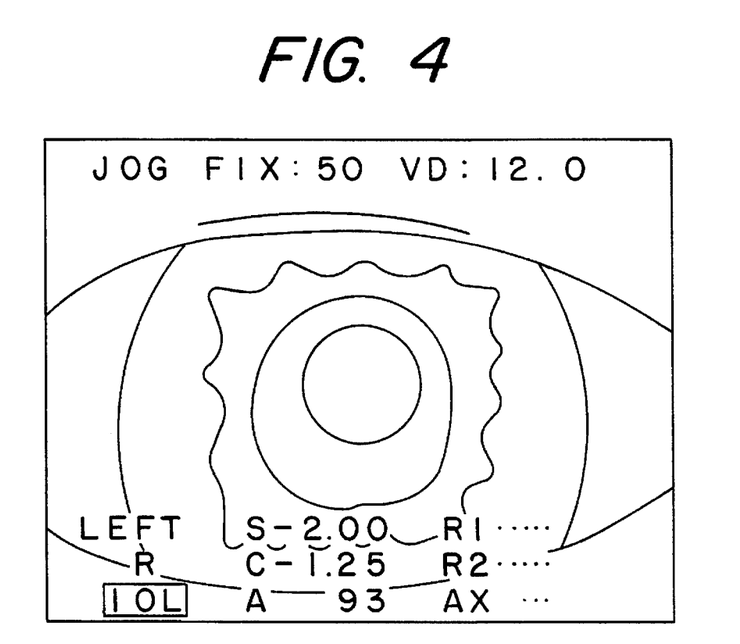
FIG. 4 is a view showing a measurement screen in a mode for measuring an eye inserted with an intraocular lens.

FIG. 4 shows the screen on the CRT monitor 5 when the IOL switch 63 is depressed from the state in FIG. 3 to change the screen to the mode for measuring an eye inserted with an intraocular lens. In this case, the jog dial 4 serves as an input means for changing the brightness of a target gazed with an eye to be examined. On the screen, "JOG FIX=50" is displayed. With this display, the examiner can see that the brightness of the target gazed with the eye to be examined can be changed by rotation of the jog dial 4. The display also indicates that the current brightness of the target is 50. In this case, when the jog dial 4 is rotated clockwise, the brightness of the target increases; when the jog dial 4 is rotated counterclockwise, the brightness of the target decreases. In this case, the setting of the brightness of the target which is required for each examiner is assumed to depend on personal differences of examiners. For this reason, after a measurement value is printed out upon depressing a print switch, the set value is restored to the initial set value prestored in the apparatus.

Figure 5:
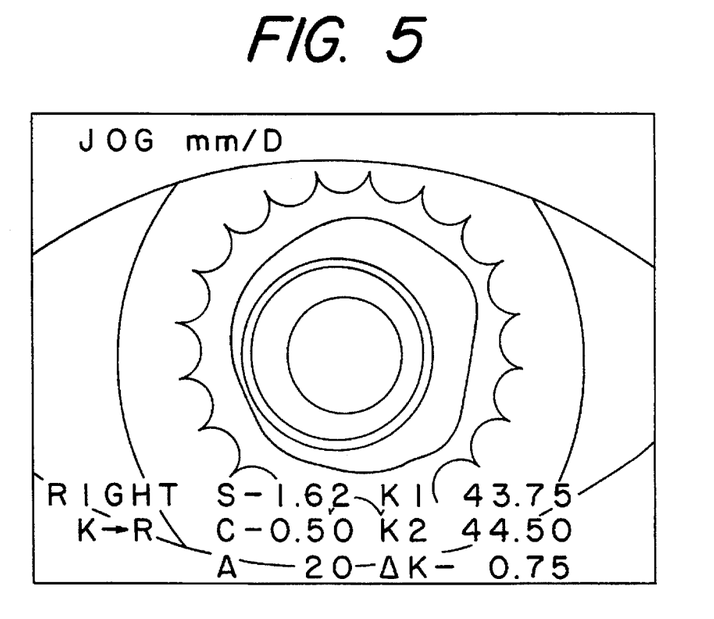
FIG. 5 is a view showing a corneal shape measurement screen.

FIG. 5 shows the screen in a mode in which the refracting power and the corneal radius of curvature are simultaneously measured. This mode can be selected by the mode switch 64. In this case, "JOG:mm/D" is displayed. This indicates that the display unit of the corneal radius of curvature can be changed from mm to Diopter during rotation of the jog dial 4, and vice versa. The examiner observes this display and recognizes that the current function of the jog dial 4 is changed to the display unit for the corneal radius of curvature.

Figure 6:
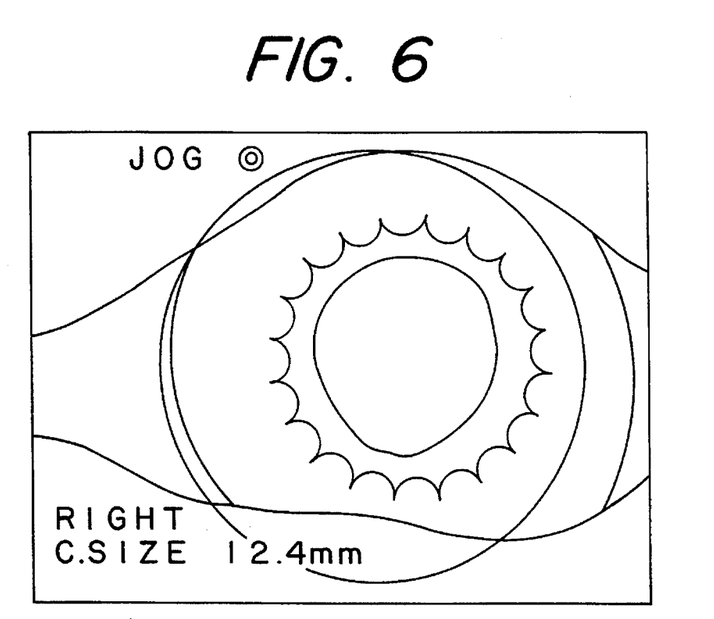
FIG. 6 is a view showing a corneal size measurement screen.

FIG. 6 shows the screen displayed when the mode switch 66 is depressed to change the screen to the corneal size measurement mode. In this mode, a circle is drawn on the screen, and the size on the concentric circle changes centering on the center of the screen upon rotation of the jog dial 4. A scale displayed on the screen also changes. After the eye to be examined is positioned to the center of the screen by the examiner, the jog dial 4 is rotated to align the corneal edge with the size of the circle on the screen. In this case, the size value corresponding to the size of the circle on the screen is displayed as a scale value at the lower left position of the screen. When the corneal edge is aligned with the circle on the screen, the examiner reads the scale value appearing at the lower left position of the screen. On the screen, JG⊙ is displayed, so the examiner can perceptually know that the size of the circle can be changed by rotation of the jog dial 4. The measurement value of this corneal size is printed out at the printer together with other measurement values in measurements of the refracting power and corneal radius of curvature.

Figure 7:
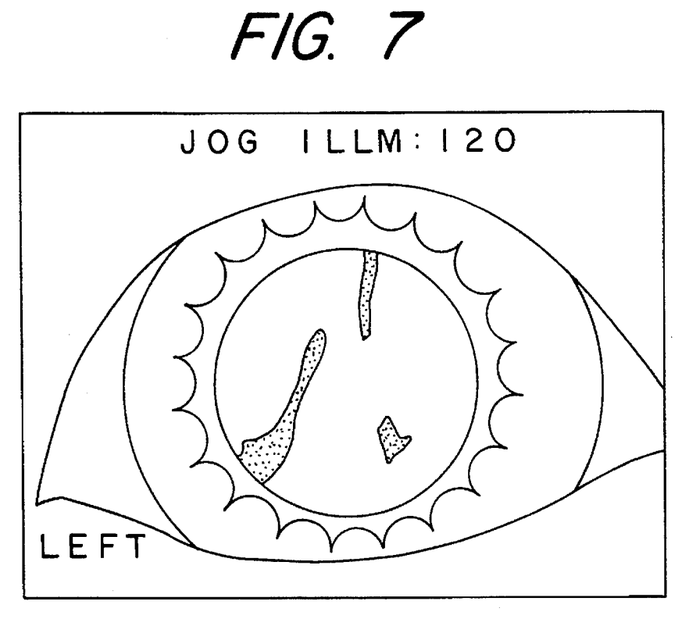
FIG. 7 is a view showing a diaphanoscopy observation screen.

FIG. 7 shows the screen obtained when the mode switch 65 is depressed to change the screen to a diaphanoscopy observation mode. Upon diaphanoscopy observation, if the illumination light amount is not properly adjusted, the eye may not be properly observed depending upon the degree of opacity of the crystal of a patient. Therefore, the examiner controls the illumination light amount by rotating the jog dial 4. The screen display in this case becomes "JOG ILLM:120", which indicates to the examiner that the illumination light amount can be changed by rotation of the jog dial 4 and that the current degree of illumination light is 120.

Figure 8:
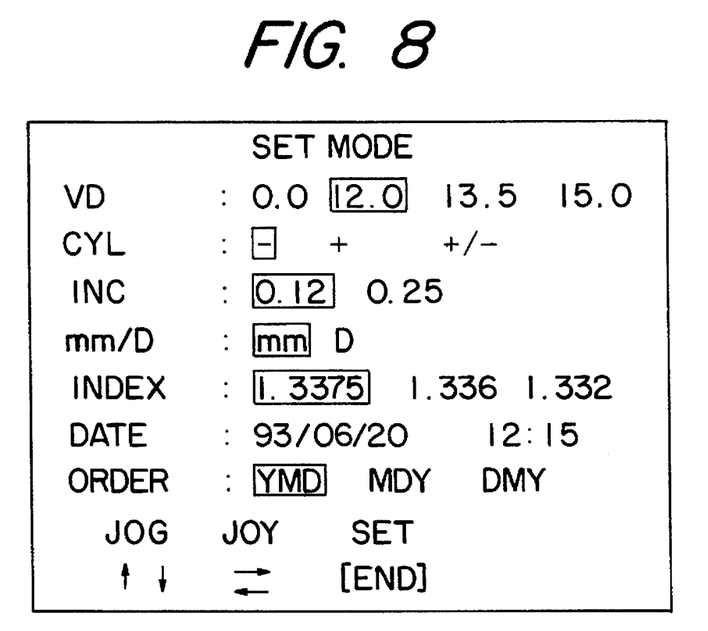
FIG. 8 is a view showing a screen for setting various measurement conditions.

FIG. 8 shows the screen set when the set switch 62 is depressed to obtain a set mode for setting various conditions. In this case, "JOG↑↓JOY←→" is displayed at the lower portion of the screen to indicate the following. When the cursor is to be vertically moved to select an item, the jog dial 4 can be rotated. When the cursor is to be horizontally moved to obtain another setting, the joystick 3 can be rotated. In practice, the main body need not be vertically moved in the set mode. Even if rotation of the joystick is used to set conditions, no practical inconvenience occurs.

Figure 9:
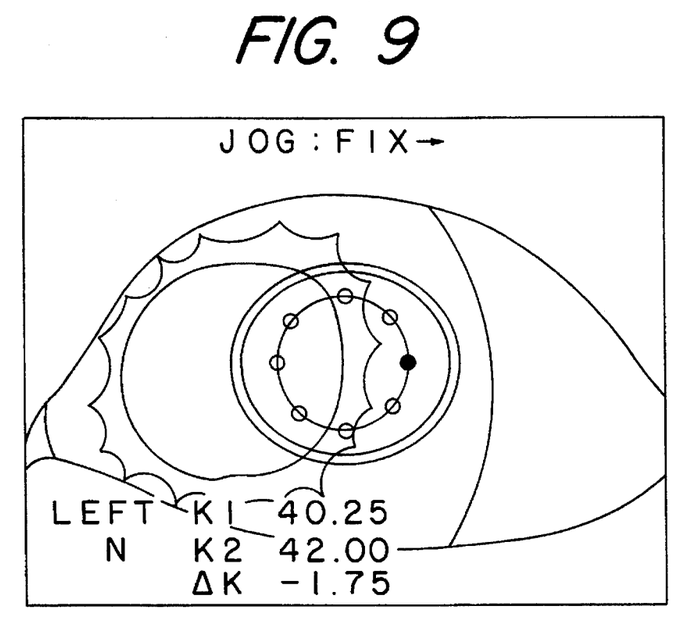
FIG. 9 is a view showing a shape measurement screen for a portion around a cornea.

FIG. 9 is a view showing a state in which the radius of curvature around the cornea is measured using the keratometer function. This keratometer function mode can be selected by the mode switch 64. This apparatus has eight target lamps (not shown) arranged around a measurement optical system for measurements around the cornea. These target lamps are selectively and properly turned on depending on measurement locations. In this case, a large ring used for aligning the eye to be examined with the apparatus and eight small circles angularly spaced apart from each other and respectively corresponding to the eight target lamps located on a circle inside the large ring are displayed on the screen. A currently ON lamp is indicated in black, while the OFF lamps are indicated in white. In this case, the jog dial 4 can be rotated to select a position at which the corresponding target lamp is turned on. "JOG:FIX←→" is displayed to indicate to the examiner that the position at which the corresponding target lamp is turned on can be selected by rotation of the jog dial 4.

Figure 10:
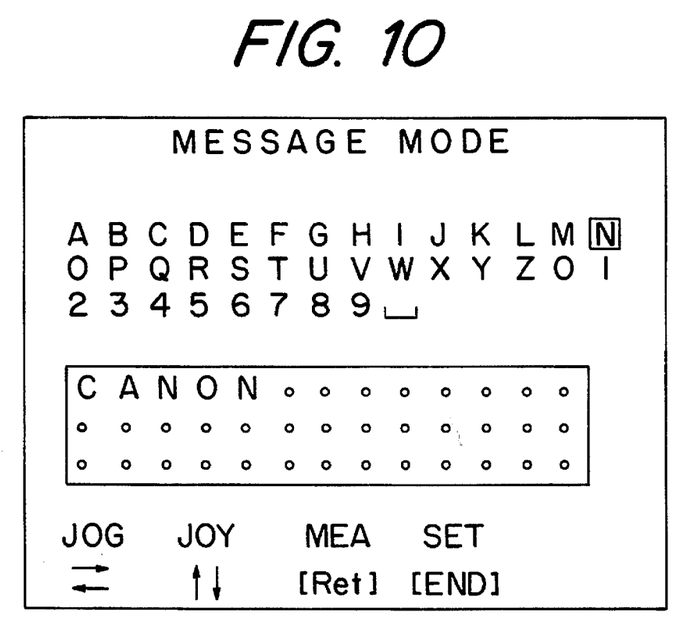
FIG. 10 is a view showing a message input screen.

FIG. 10 is a view in a message mode. This function is to output a hospital name, a patient's name, and the like. In this case, letters and numbers in the upper portion in FIG. 10 are selected and a measurement switch is depressed to register letters in a lower display space. In this case, the cursor can be moved horizontally with the jog dial 4 and vertically with the joystick 3, thereby quickly shifting the cursor to the letter of interest. In this case, "JOG←→JOY↑↓" is displayed in the lower portion of the screen as opposed to the display in FIG. 8.

Figure 11:
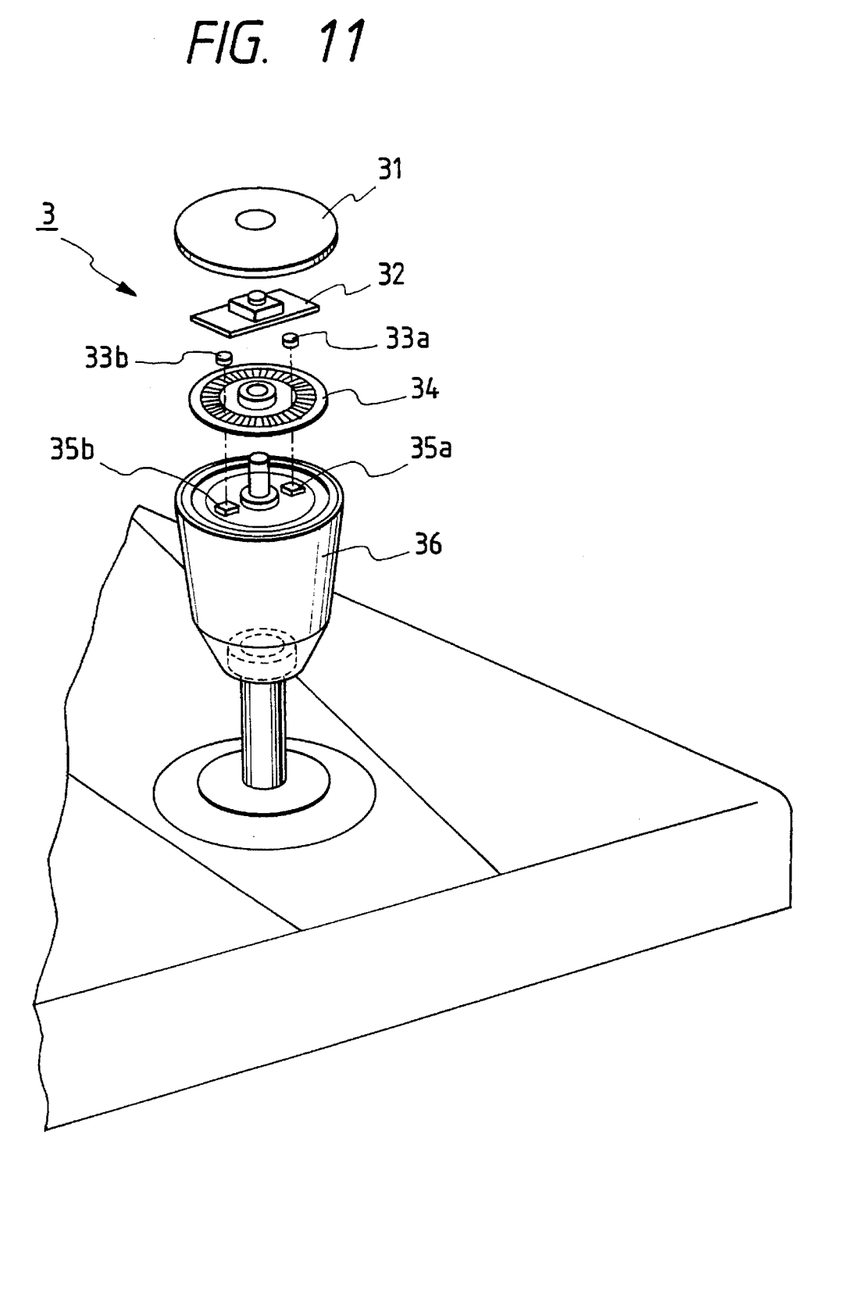
FIG. 11 is a view showing the structure of a joystick.

FIG. 11 shows the structure of the joystick 3. The joystick 3 comprises an upper lid 31, a measurement switch 32, encoder LEDs 33a and 33b, a rotary encoder scale 34, detection photodetectors (PDs) 35a and 35b, and a main cover 36. The rotary encoder scale 34 is fixed to the main cover 36 and is rotated together with the main cover 36 upon rotation of the main cover 36. The measurement switch 32, the encoder LEDs 33a and 33b, and the detection PDs 35a and 35b are arranged not to be rotated together with the main cover 36. The rotational direction and speed of the main cover can be detected in accordance with the speeds of light pulses incident on the detection PDs 35a and 35b, and a phase difference between the PDs. Outputs from the detection PDs 35a and 35b serve as outputs from the rotary encoder.

Figure 12:
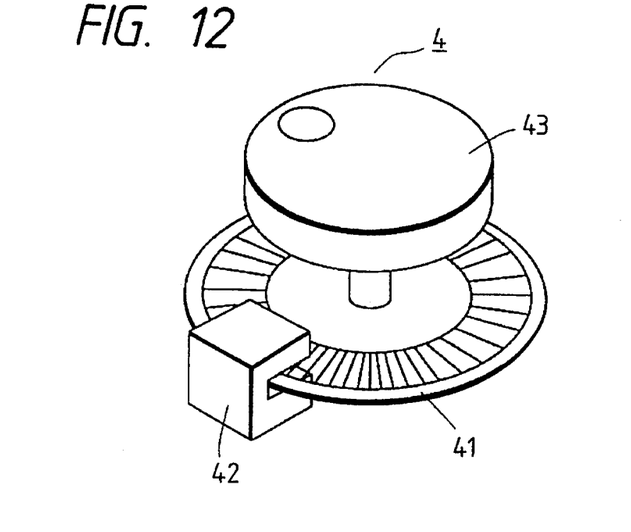
FIG. 12 is a view showing the structure of a jog dial.

FIG. 12 shows the structure of the jog dial 4. The jog dial 4 comprises a rotary encoder scale 41, a photointerrupter 42 integrally incorporating an LED and a PD, and a knob 43. Detection of rotation by the rotary encoder is almost the same as that in the joystick 3.

Figure 13:
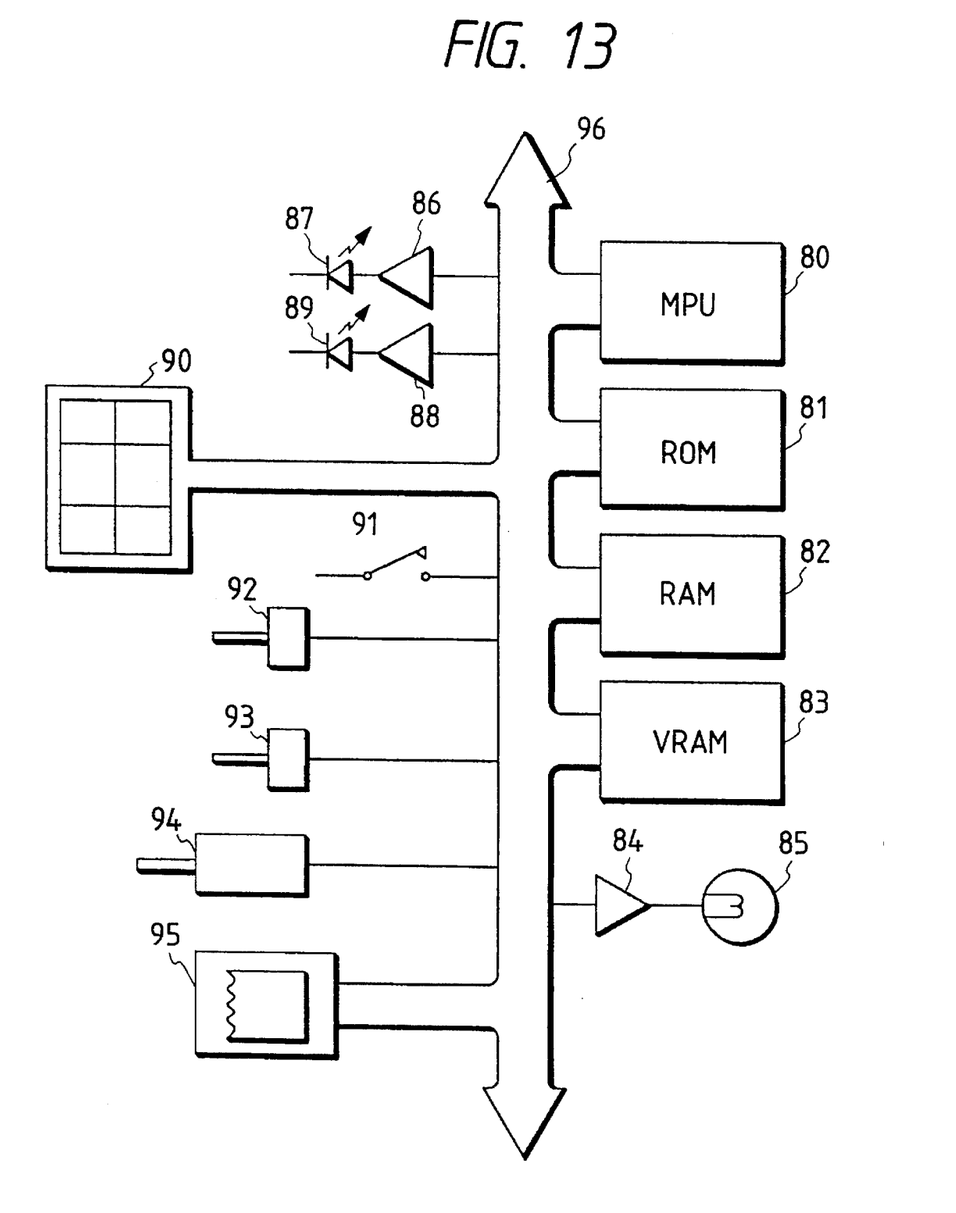
FIG. 13 is a block diagram showing the overall electrical circuit.

FIG. 13 is a block diagram showing the overall circuit arrangement. An MPU 80 controls overall operations in accordance with programs stored in a ROM 81. The MPU 80 controls peripheral devices through a data bus 96. A target lamp 85, an autorefracting power measurement source and diaphanoscopy observation light source 87, and a keratometer measurement LED 89 variably control the brightness by controlling the corresponding drivers through D/A converters 84, 86, and 88, respectively. Vertical movement is performed such that rotation of the joystick is detected by a rotary encoder 93 as described above to drive a vertical movement pulse motor 94. Rotation of the jog dial 4 is detected by a jog dial rotary encoder 92 to perform various functions in accordance with a set mode. A VRAM 83 is a bit map memory for displaying a figure on a CRT monitor. Predetermined data is written at a predetermined address in accordance with each set mode under the control of the MPU 80 to display a character, mark, scale, cursor or the like on the screen. The MPU 80 also detects a switch panel 90, a printer 95 for printing out measurement values, and a measurement switch 91 arranged on the joystick.

As in this embodiment, the joystick or the rotary mechanism arranged independently of the joystick performs different operations depending on the set mode, thereby reducing the number of switches and cost. In addition, the user need not operate a large number of switches. The joystick or knob is rotated to select an item from a large number of items or an optimal state of a plurality of continuously changing states, thereby improving operability. In addition, the current function of the rotary mechanism is displayed on the display means arranged in the main body, so that the user can easily confirm the function of the switch, thereby reducing the possibility of erroneous operations.

Figure 14:
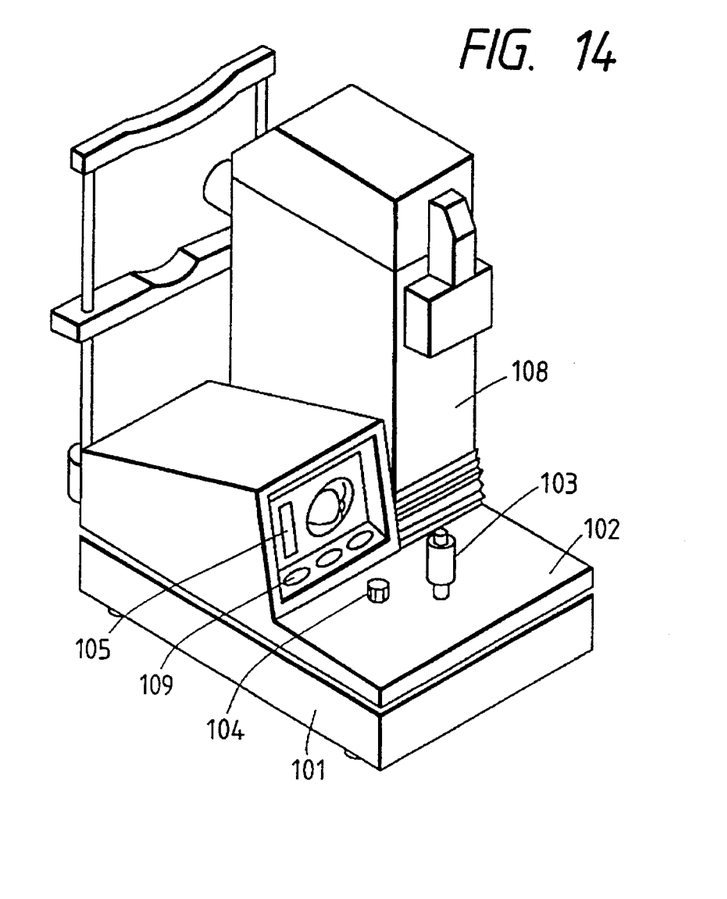
FIG. 14 is a perspective view showing a nonscattering pupil fundus camera according to another embodiment of the present invention.

FIG. 14 is a perspective view showing another embodiment of the present invention. This embodiment is an application to a nonscattering pupil fundus camera. The main body comprises a stationary portion 101 and a movable portion 102 as in FIG. 1. The movable portion 102 has a joystick 103. An illumination light amount change knob 104 is arranged near the joystick 103. In a normal application state, rotation of the joystick is controlled to vertically move a camera portion 108 as in the previous embodiment. Positioning with an eye to be examined is performed while observing a CRT monitor 105. Switches 109 arranged on the front surface of the CRT monitor 105 are used to set various conditions. The knob 104 is controlled to change the observation illumination light amount with its angular position.

Figure 15:
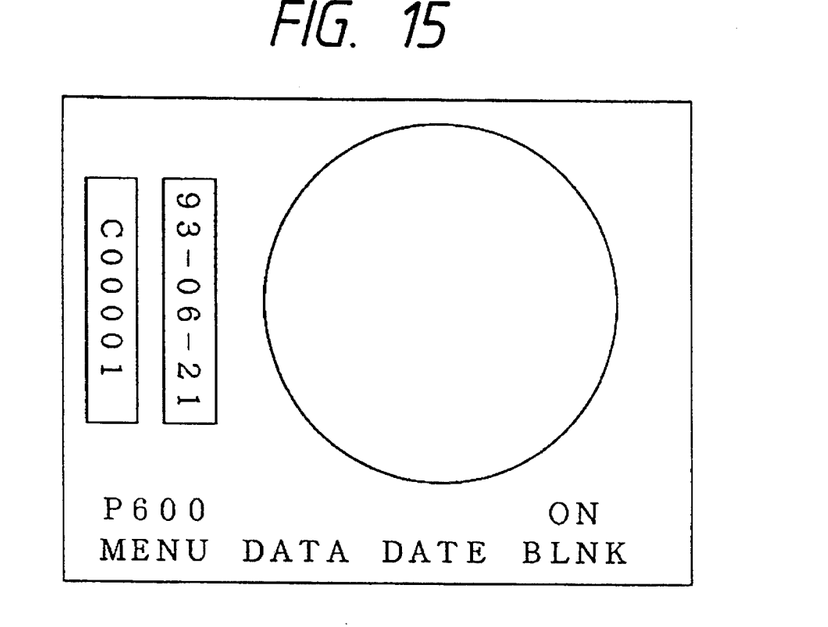
FIG. 15 is a view showing a screen in a normal fundus photographing mode.
Figure 16:
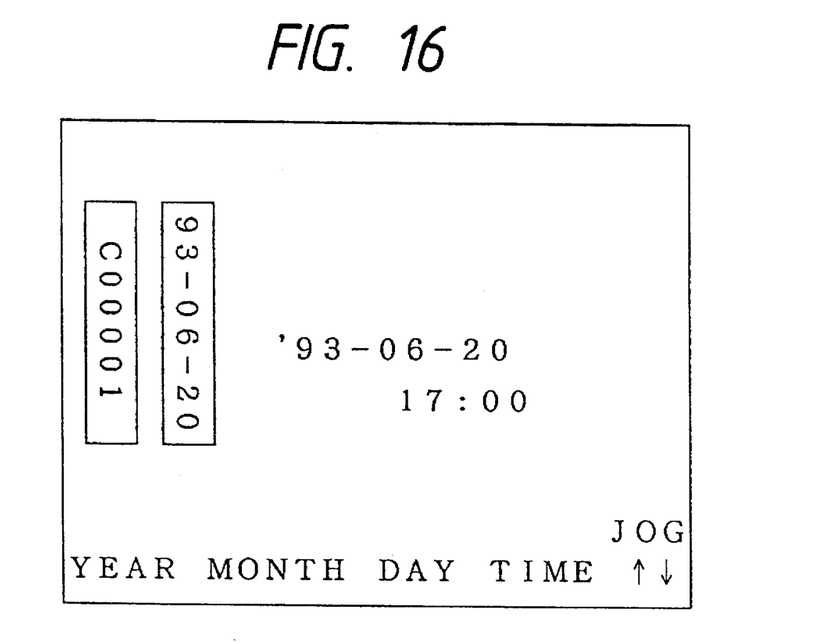
FIG. 16 is a view showing a date input screen.

FIG. 15 shows the screen in a normal photographing mode. Control items corresponding to the switches 109 are displayed in the lower portion of the screen. FIG. 16 shows the screen in the date setting mode. In this case, the switches 109 are depressed to change any one of the date and time. The knob 104 is rotated to change the numeric value of the selected item. "JOG↑↓" indicates that the function of the knob 104 actually changes numerical values, thereby preventing erroneous operations.

As has been described above, in each embodiment described above, the number of switches can be reduced, easy operation is assured and operability is improved. In addition, a function is displayed on the display means to prevent erroneous operations.

What is claimed is:

1. An ophthalmic apparatus comprising:
   an apparatus control mechanism for performing an ophthalmic operation for an eye to be examined, said control mechanism having multiple modes; and
   a rotary mechanism for inputting information to said control mechanism, said rotary mechanism serving as input means for performing different control operations respectively corresponding to each of the modes.

2. An apparatus according to claim 1, further comprising display means for displaying information associated with an input function in a current mode of said rotary mechanism.

3. An apparatus according to claim 2, wherein said display means also displays an anterior eye portion of the eye to be examined.

4. An apparatus according to claim 1, wherein said rotary mechanism comprise a dial, arranged near a joystick, for positioning said apparatus with the eye to be examined.

5. An apparatus according to claim 1, wherein said control mechanism has an eye refracting power measurement mode.

6. An apparatus according to claim 5, wherein said rotary mechanism serves as input means for controlling a change in distance between vertices in the eye refracting power measurement mode.

7. An apparatus according to claim 1, wherein said control mechanism has a mode for measuring an eye inserted with an intraocular lens.

8. An apparatus according to claim 7, wherein said rotary mechanism serves as input means for controlling a change in brightness of a target in the mode for measuring the eye inserted with the intraocular lens.

9. An apparatus according to claim 1, wherein said control mechanism has a mode for measuring a corneal radius of curvature.

10. An apparatus according to claim 9, wherein said rotary mechanism serves as input means for controlling to switch a display unit of the corneal radius of curvature.

11. An apparatus according to claim 1, wherein said control mechanism has a corneal size measurement mode.

12. An apparatus according to claim 11, wherein said rotary mechanism serves as input means for controlling to change a radius of a circle displayed together with an anterior eye image on a screen arranged in said apparatus.

13. An apparatus according to claim 1, wherein said control mechanism has an diaphanoscopy observation mode.

14. An apparatus according to claim 13, wherein said rotary mechanism serves as input means for controlling to change an illumination light amount to the eye to be examined in the diaphanoscopy observation mode.

15. An apparatus according to claim 1, wherein said control mechanism has a mode for setting various apparatus conditions.

16. An apparatus according to claim 15, wherein said rotary mechanism serves as input means for controlling to move a cursor on a screen arranged in said apparatus in the mode for setting the various apparatus conditions.

17. An apparatus according to claim 1, wherein said control mechanism has a keratometer function mode.

18. An apparatus according to claim 17, wherein said rotary mechanism serves as input means for controlling to change a position of an ON target lamp in the keratometer function mode.

19. An apparatus according to claim 1, wherein said control mechanism has a message mode for setting a message added to an output when ophthalmic data is output.

20. An apparatus according to claim 19, wherein said rotary mechanism serves as input means for controlling to move a cursor on a screen arranged in said apparatus in the message mode.

21. An apparatus according to claim 1, wherein said control mechanism has a mode for photographing a fundus of the eye to be examined.

22. An apparatus according to claim 21, wherein said rotary mechanism serves as input means for controlling vertical movement of a camera portion for photographing the fundus of the eye to be examined in the fundus photographing mode.

23. An apparatus according to claim 1, wherein said control mechanism has a date setting mode.

24. An apparatus according to claim 23, wherein said rotary mechanism serves as input means for controlling to change a numerical value for setting a date.

25. An apparatus according to claim 1, further comprising a plurality of mode selection switches.

26. An apparatus according to claim 1, wherein said rotary mechanism constitutes an arrangement for inputting information upon rotation of a joystick so as to position said apparatus with respect to the eye to be examined.

* * * * *

UNITED STATES PATENT AND TRADEMARK OFFICE
CERTIFICATE OF CORRECTION

PATENT NO. : 5,500,696
DATED : March 19, 1996
INVENTOR(S) : TAKASHI MASUDA, ET AL.

It is certified that error appears in the above-indentified patent and that said Letters Patent is hereby corrected as shown below:

ON THE COVER PAGE:
  [56] References Cited

"5,203,979 4/1994 Maeda et al." should read --5,302,979 4/1994 Maeda et al.--.

COLUMN 5:

Line 56, "comprise" should read --comprises--.

COLUMN 6:

Line 18, "an" should read --a--.

Signed and Sealed this

Fifth Day of November, 1996

Attest:

BRUCE LEHMAN

Attesting Officer        Commissioner of Patents and Trademarks